United States Patent [19]

Shea et al.

[11] 4,292,693

[45] Oct. 6, 1981

[54] LOCKING BAIL STAPEDIAL PROSTHESIS

[75] Inventors: John J. Shea, Shelby County; Calvin Griggs, Memphis, both of Tenn.

[73] Assignee: Richards Manufacturing Company, Inc., Memphis, Tenn.

[21] Appl. No.: 82,195

[22] Filed: Oct. 5, 1979

[51] Int. Cl.³ ........................... A61F 1/24; A61F 1/18
[52] U.S. Cl. ........................................................ 3/1.9
[58] Field of Search .............................. 3/1, 1.9, 1.91; 292/246; 16/126

[56] References Cited

U.S. PATENT DOCUMENTS

| | | | |
|---|---|---|---|
| 987,579 | 3/1911 | Koenig et al. | 16/126 X |
| 1,681,587 | 8/1928 | Kielberg | 292/246 X |
| 3,196,462 | 7/1965 | Robinson | 3/1 |
| 3,711,869 | 1/1973 | Shea, Jr. | 3/1 |
| 3,800,934 | 4/1974 | Decker | 292/246 X |
| 3,931,648 | 1/1976 | Shea, Jr. | 3/1.9 |

FOREIGN PATENT DOCUMENTS 204496 12/1967 U.S.S.R. ....................................... 3/1

Primary Examiner—Clifford D. Crowder
Attorney, Agent, or Firm—Robert D. Yeager

[57] ABSTRACT

An improvement in bail-and-bucket, piston-type stapedial prostheses in which the bail is pivotally mounted to rotate about the open end of the bucket. Means are provided on the bucket for permitting overcenter pivotal movement of the bail in one direction and thereafter preventing overcenter pivotal movement of the bail in the opposite direction. The preferred means for accomplishing this function is an opposed pair of cam surfaces mounted on the bucket.

8 Claims, 8 Drawing Figures

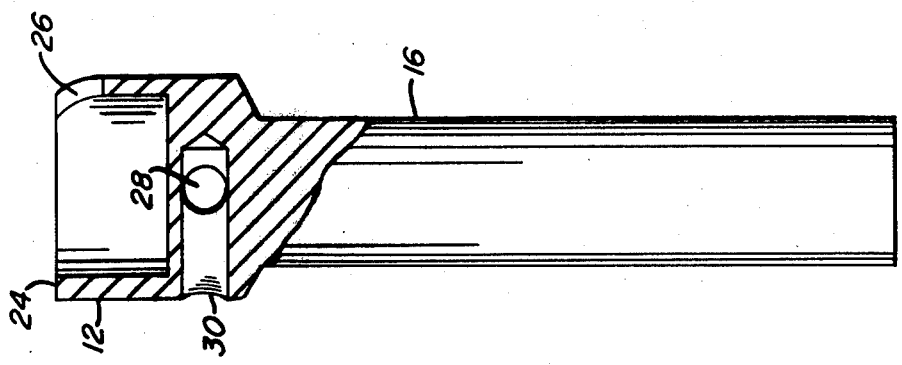
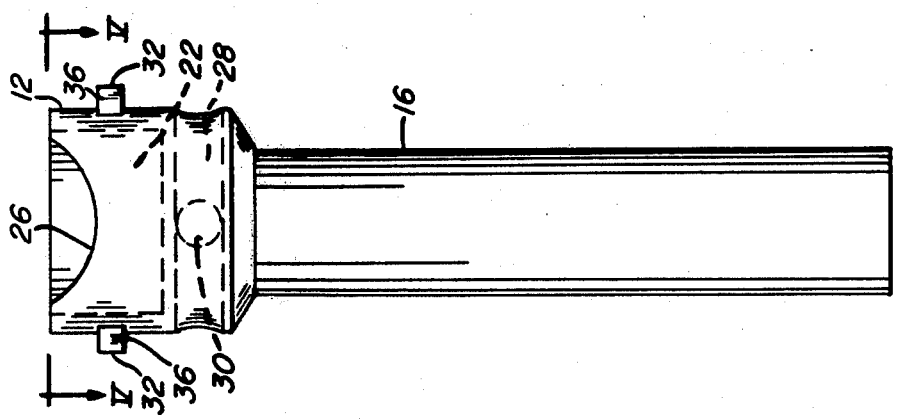
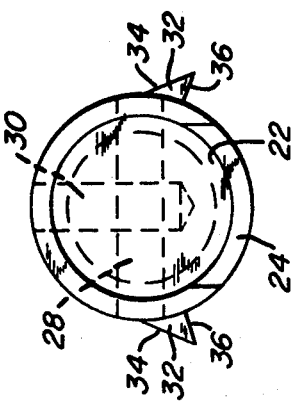

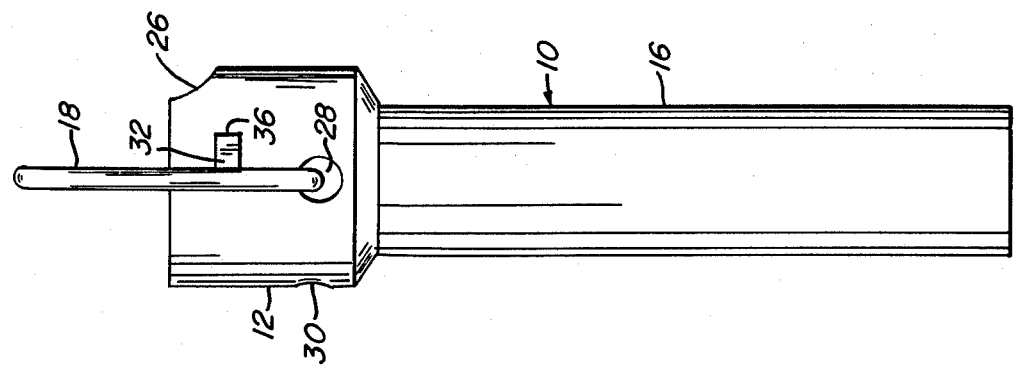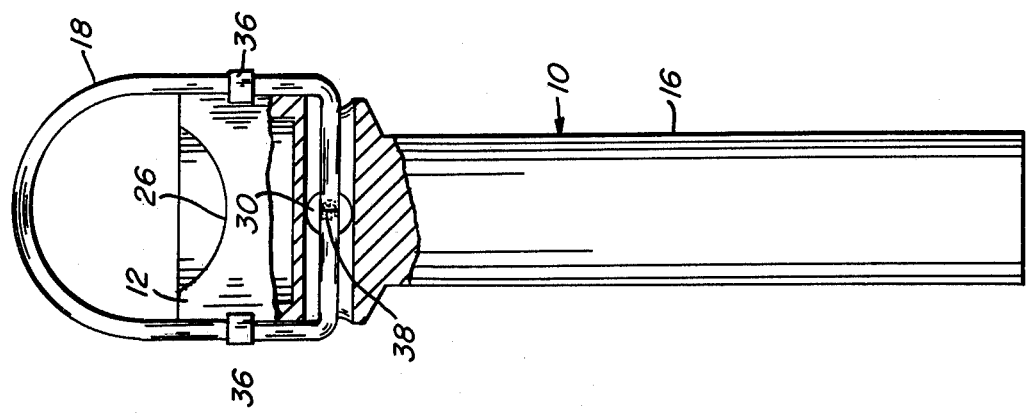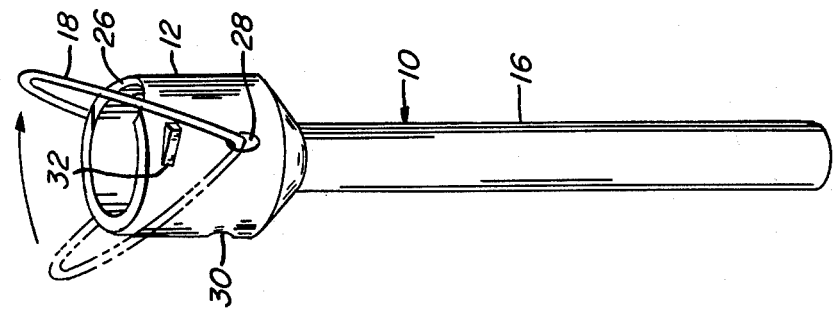

LOCKING BAIL STAPEDIAL PROSTHESIS

BACKGROUND OF THE INVENTION

1. Field of the Invention

This invention relates to otic prostheses; more particularly to an improved stapedial prosthesis.

2. Description of the Prior Art

Reconstruction of the sound-conducting mechanism of the middle ear by surgical implantation of biocompatible prostheses is well-known. FIG. 1 of the drawings is a schematic representation of the natural mechanism for transmitting vibrations of the eardrum (tympanum) to the sound-producing organs of the inner ear which are located behind the aperature (oval window) between the middle and inner ears. The mechanism includes three tiny bones called the malleus, the incus and the stapes, which move in response to the vibration of the tympanum. The stapes, in particular, extends from the lenticular process of the incus to the oval window and moves in piston-like fashion to transmit sound vibrations from the incus to the oval window.

When the stapes becomes diseased, it may be removed and a stapedial prosthesis may be implanted in its place, all by well-known surgical techniques. One of the most widely-used stapedial prostheses is a piston-like member formed of stainless steel, "Teflon" (a registered trademark of DuPont for a tetrafluoroethylene-hexaflorapropylene copolymer), polyethylene or other biocompatible material. Such prostheses are illustrated in U.S. Pat. Nos. 3,196,462; 3,711,869; and 3,931,684, for example and typically include a bucket (or socket) at one end for receiving a portion of the lenticular process of the incus and a cylindrical rod portion at the other end for engaging the oval window (or a vein graft positioned thereover by the surgeon).

A problem associated with stapedial prostheses of this type is providing means for quickly and predictably securing the bucket end of the prosthesis to the lenticular process of the incus in a manner to (i) avoid the occurrence of pressure necrosis, which may result from the securement being too tight and (ii) prevent loosening of the securement, which may result in the prosthesis becoming dislodged after implantation and thereafter extruding within the middle ear. U.S. Pat. Nos. 3,711,869 and 3,931,648 address this problem and provide certain alternatives to the use of a wire bail as the means of securement disclosed in U.S. Pat. No. 3,196,462. The wire bail prosthesis offers certain advantages in stapedial replacement surgery, however, primarily the ease with which the prosthesis may be introduced; therefore, persons skilled in the art would like to continue to use the bail-and-bucket prosthesis if the above-mentioned problems could be overcome.

The bail, (or handle) of a bail-and-bucket, piston-type prosthesis is oriented by the surgeon so that its axis of pivotal rotation generally is horizontal. With the prosthesis in that orientation, the bail is rotated in an upward arc, past the horizontal, until the bail contacts the long process of the incus. Only the frictional engagement of the bail against the incus holds the bail in place. If the bail should rotate downwardly, out of range of contact with the incus, the prosthesis may become dislodged and extrusion may result.

SUMMARY OF THE INVENTION

The present invention overcomes the lack of predictability of bail orientation associated with known bail-and-bucket stapedial prostheses by providing means for locking the bail after it is moved by the surgeon past the vertical position, thereby preventing the bail from falling away from the incus in a downward arc. Free pivotal movement of the bail in an upward arc is provided (and indeed is necessary) to permit the surgeon first to position the prosthesis with respect to the lenticular process of the incus and the oval window while the bail is in the insertion position and out of the way, and then to allow the surgeon to rotate and lock the bail in an upward arc into engagement with the long process of the incus. As the bail traverses its upward arc, it passes through the midpoint thereof, which is approximately at the horizontal, and goes "over-center". Means provided as part of the present invention on the bucket portion of the prosthesis prevents the bail after being locked in place from traversing the reverse arcuate path to go back "overcenter" and fall away from the incus.

The present invention provides, accordingly, in a prosthesis for replacing the stapes of the middle ear, the prosthesis being of the piston type and having a bucket end portion for receiving a portion of the lenticular process of the incus and a bail mounted to pivot about the open end of the bucket portion, the improvement comprising: means mounted on the bucket portion for permitting overcenter pivotal movement of the bail in one direction and thereafter preventing overcenter pivotal movement of the bail in the opposite direction. Preferably, the means for permitting and thereafter preventing overcenter pivotal movement of the bail includes at least one and preferably a pair of cam surfaces oppositely mounted on the bucket portion. Still further preferably, each of the cam surfaces tapers outwardly from the surface of the bucket portion in the direction the overcenter pivotal movement of the bail is permitted and terminates in an inwardly extending shoulder portion which engages the bail to prevent the overcenter pivotal movement thereof in the opposite direction.

In the preferred embodiment of the present invention, the portion of the bail that pivots about the bucket portion is a resilient, U-shaped member adapted to deform for passage over the tapered cam surfaces and resume its shape for engagement against the shoulder portions. The bucket portion of the present invention includes a rim defining the open end of the bucket portion, and the rim may have an inwardly extending opening, preferably arcuate in shape, to minimize pressure on the lenticular process of the incus when the bucket portion is in place thereon. The present invention also may include a radially extending bore in the bucket portion, which bore is adapted to receive end of a surgical instrument for manipulation of the prosthesis.

Other features and advantages of the present invention will become apparent as the following detailed description, taken with the accompanying drawings, proceeds.

BRIEF DESCRIPTION OF THE DRAWINGS

FIG. 3 is a side view, partially in section with parts removed, of the piston portion of the present invention;

FIG. 4 is an end view of the piston shown in FIG. 3;

FIG. 5 is a top plan view of the piston of FIG. 4 taken at line V—V thereof;

FIG. 6 is a side elevational view of the prosthesis of the present invention;

FIG. 7 is an end view partially in section with parts removed, of the prosthesis shown in FIG. 6; and FIG. 8 is a prospective view of the prosthesis of the present invention.

DESCRIPTION OF THE PREFERRED EMBODIMENTS

Figure 1:
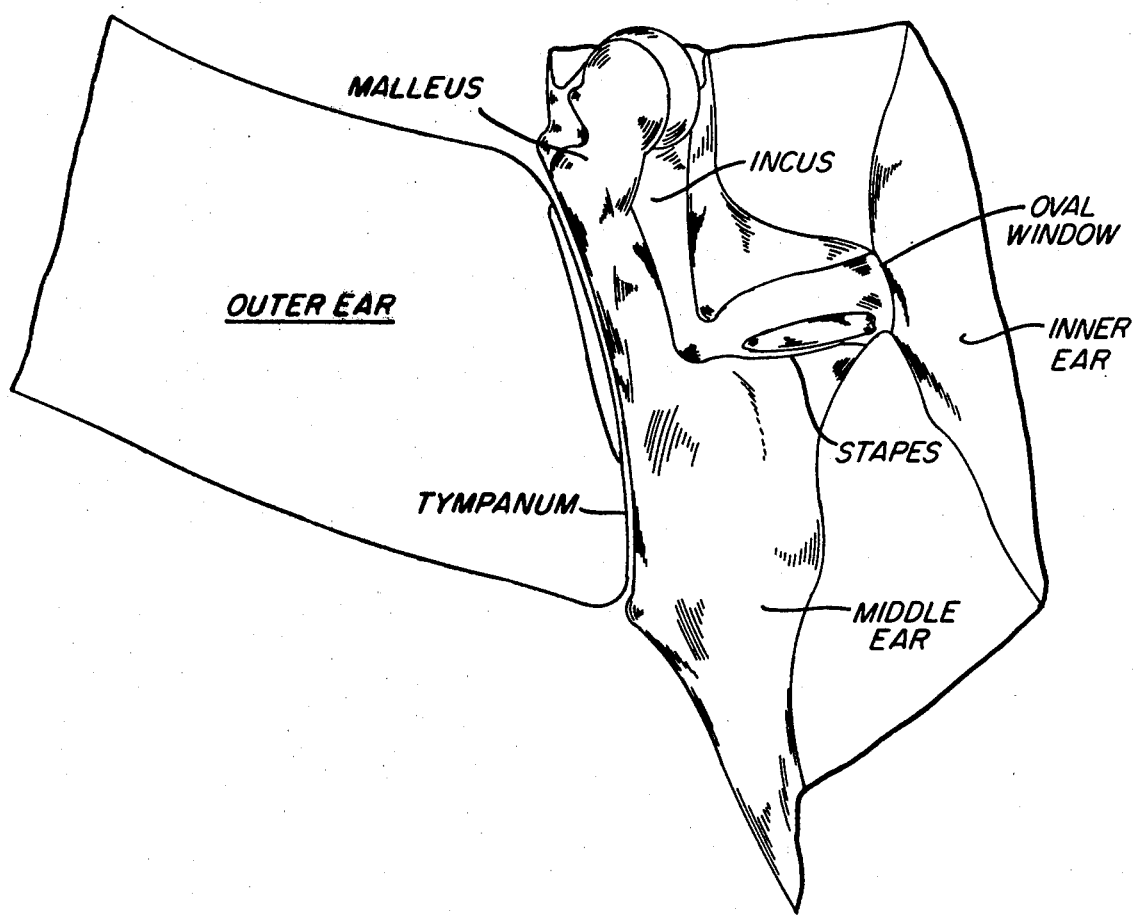
FIG. 1 is a diagram illustrating the sound-transmitting mechanism of a human ear.
Figure 2:
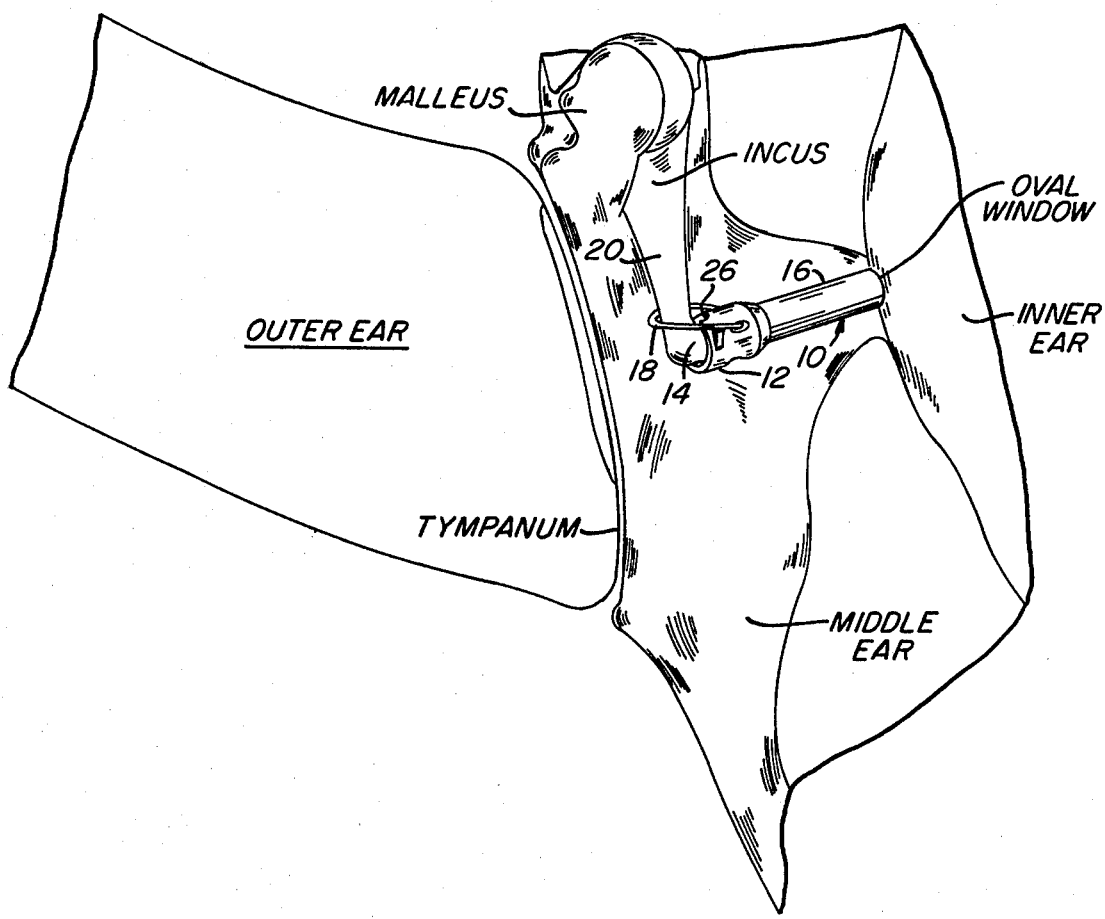
FIG. 2 is similar to FIG. 1 with the stapes removed and an embodiment of the present invention substituted therefor.

Referring to the drawings, particularly to FIG. 2, there is shown a stapedial prosthesis 10 of the present invention surgically implanted in the middle ear after removal of the stapes. Prosthesis 10 includes a bucket portion 12 having received therein a portion of the lenticular process 14 of the incus and a rod portion 16 whose free end engages the oval window. Pivotally mounted on bucket portion 12 is a wire bail 18 which, after positioning prosthesis 10, is rotated to the position shown in loose engagement with the long process 20 of the incus. Prosthesis 10 implanted in this manner transmits sound vibrations from the incus to the oval window of the middle ear.

Prosthesis 10 will be described now in greater detail by reference first to FIGS. 3–5 which show the piston portion of prosthesis 10. Bucket portion 12 and rod portion 16 comprise the piston portion of prosthesis 10; these parts generally are integrally formed from a single piece of stainless steel, Teflon or other biocompatible material including a high molecular weight polyethylene sponge marketed by Richards Manufacturing Company, Inc., Memphis, Tenn. under the trademark "Plastipore TM". Plastipore TM porous polyethylene is highly non-reactive with body tissue and is 70 to 90% porous with an average pore size of 20 to 40 microns; this construction may encourage tissue ingrowth which is used to advantage in stapes replacement surgery. Plastipore TM porous polyethylene is relatively rigid and thus lends itself to the machining necessary to form the piston portion of prosthesis 10.

Bucket portion 12 preferably is cylindrical and has its longitudinal axis aligned with the longitudinal axis of rod portion 16. A cylindrical recess 22 is formed in bucket portion 12 to receive a portion of the lenticular process of the incus. The portion of wall 24 of bucket portion 12 that is intended to rest on the top surface of the lenticular process of the incus after implantation has formed in its rim an inwardly extending, arcuate-shaped, notch 26. The purpose of notch 26 is to provide more tolerance in fitting bucket portion 12 over the end of the lenticular process of the incus and thereby minimize the risk of pressure necrosis.

Bucket portion 12 has formed therein, on a diameter parallel to the major chord of notch 26, a bore 28 which extends completely through bucket portion 12. Bore 28 is used to anchor bail 18 in a manner described hereinbelow. A second bore 30 is formed in bucket portion 12 transversely to and its axis may be in the same plane as bore 28. In the illustration of FIG. 3 bore 30 extends radially inwardly slightly beyond the junction with bore 28. The opening of bore 30 is located in bucket portion 12 on the opposite site from notch 26 and is used to receive the end of a surgical instrument, for example a right angle pick, for manipulation of prosthesis 10.

Mounted on opposite sides of bucket portion 12, generally on the same diameter as bore 28, are cams 32. Each of cams 32 tapers smoothly outwardly, from a point generally in the vertical plane containing the axis of bore 28, in the direction away from the opening of bore 30 and generally toward notch 26. The tapered surfaces 34 of cams 32 are at a convenient angle of about 22° from the tangential plane of bucket 12, as best shown in FIG. 5; each tapered surface terminates abruptly in an inwardly extending shoulder 36 forming a convenient angle of about 15° with the horizontal. The purpose of cams 32 is to permit passage of bail 18 in pivoting toward notch 26 but, after such passage, to prevent return pivotal movement of bail 18 as will be described hereinafter. For purposes of convenience in illustration, cams 32 are located in FIG. 6 such that bail 26 appears in a vertical position when rotated past cams 32. In a preferred embodiment, cams 32 are located on bucket 12 such that bail 26 assumes an angle of about 10° past the vertical when rotated past the cams to the locked position.

In typical dimensions: the rod portion 16 may range between about 3.5 mm to 5.0 mm in length and between about 0.4 mm and 1.0 mm in diameter; the inside diameter of recess 22 is about 1.0 mm and the height of bucket portion is about 1.0 mm; the diameter of bores 28 and 30 is about 0.25 mm and notch 26 has a radius of about 0.5 mm.

Turning now to FIGS. 6–8, the locking bail of the present invention will be described now. Bail 18 may be formed of any suitable biocompatible material that may be formed into a generally elongated U-shaped configuration with ends turned inwardly at right angles and retain that configuration, but bail 18 preferably will be 316 L stainless steel wire having a diameter of about 0.1 mm. As best shown in FIG. 7 bail 18 is preferably formed of a single strand of wire with its ends joined in abutting relationship as by weld 38. The material of bail 18 is such that one end may be deformed and inserted completely through bore 28 so that weld 38 may be made; thereafter weld 38 is pulled into bore 28 until it is approximately centered and the deformed portion resumes its original shape. Although bail 18 is shown in the drawings as being pivotally mounted to bucket portion 12 by the means just described, a variety of well-known mounting techniques may be utilized to provide the necessary pivotal movement of bail 18 with respect to bucket portion 12.

Referring specifically to FIG. 8, the operation of prosthesis 10 will be described now. After the surgeon removes the stapes and performs the necessary steps preparatory to implantation of the prosthesis of the present invention, including covering the oval window with a graft of his choice, prosthesis 10 is inserted into position using a forcep and can be manipulated by use of bore 30 as described above. In proper orientation, recess 26 will be located on the top of lenticular process 14 of the incus (see FIG. 2) with a portion of the lenticular process inserted into recess 22 of bucket portion 12. During the insertion procedure, bail 18 is rotated to the side of bucket portion 12 having the opening the bore 30 (the position shown in dashed lines in FIG. 8). The surgeon then rotates bail 18 upwardly (in the direction indicated by the arrow in FIG. 8) so that bail 18 passes through a plane containing both bail 18 and the longitudinal axis of prosthesis 10 (a position which may be denominated "center") and moves further upwardly ("overcenter"). This movement requires bail 18 to pass over surfaces 34 of cams 32 and thus bail 18 must be sufficiently resilient to deform for this purpose. Upon reaching the end of tapered surfaces 34, bail 18 resumes its original shape (best shown in FIG. 7) with its sides substantially parallel and closely adjacent bucket portion 12. The surgeon continues the upward rotation of bail 18, if necessary, until it is in proper position surrounding long process 20 of the incus. Any downward rotation of bail 18 now is prevented because of the stop means provided by shoulders 36 of cams 32. Thus, any tendency of bucket portion 12 to become dislodged from its engagement with lenticular process 14 of the incus will be curbed by the locking action of bail 18 and shoulders 36.

Those skilled in the art may recognize that a single cam 32 may perform the same locking of bail 18 as the pair of cams 32 shown in the drawings. Such an arrangement is encompassed by the present invention but a pair of opposed stops are preferred for reasons of mechanical expediency and reliable performance.

What is claimed is:

1. In a prosthesis for replacing the stapes of the middle ear, said prosthesis being of the piston type and having a bucket end portion for receiving a portion of the lenticular process of the incus and a bail mounted to pivot about the open end of said bucket portion, the improvement comprising:
   means mounted on said bucket portion for permitting overcenter pivotal movement of said bail in one direction and thereafter preventing overcenter pivotal movement of said bail in the opposite direction.

2. The improvement recited in claim 1 wherein:
said means for permitting and thereafter preventing said overcenter pivotal movement of said bail includes at least one cam surface mounted on said bucket portion.

3. The improvement recited in claim 2 wherein:
said cam surface tapers outwardly from the surface of said bucket portion in the direction said overcenter pivotal movement of said bail is permitted and terminates in an inwardly extending shoulder portion which engages said bail to prevent said overcenter pivotal movement thereof in the opposite direction.

4. The improvement recited in claim 3 wherein:
there is present an opposed pair of said cam surfaces.

5. The improvement recited in claim 4 wherein:
the portion of said bail that pivots about said bucket portion is a resilient, U-shaped member adapted to deform for passage over said tapered cam surfaces and resumes its shape for said engagement against said shoulder portions.

6. The improvement recited in claim 1 wherein:
said bucket portion includes a rim defining said open end of said bucket portion, said rim having an inwardly extending opening.

7. The improvement recited in claim 6 wherein:
said inwardly extending opening is arcuate-shaped.

8. The improvement recited in claim 1 wherein:
said bucket portion includes a radially extending bore adapted to receive the end of a surgical instrument for manipulation of said prosthesis.

* * * * *